United States Patent [19]

Ponticello et al.

[11] Patent Number: 5,395,933
[45] Date of Patent: Mar. 7, 1995

[54] CARBAMAZEPINE HAPTEN ANALOGUES

[75] Inventors: Ignazio S. Ponticello; Mohan S. Saini, both of Pittsford, N.Y.

[73] Assignee: Eastman Kodak Company, Rochester, N.Y.

[21] Appl. No.: 926,205

[22] Filed: Aug. 7, 1992

[51] Int. Cl.$^6$ .............................................. C07D 223/22
[52] U.S. Cl. .................................. 540/589; 540/575; 540/553
[58] Field of Search .................. 540/575, 589, 553

[56] References Cited

U.S. PATENT DOCUMENTS

| | | | |
|---|---|---|---|
| 3,518,268 | 6/1970 | Adank et al. | 540/575 |
| 4,255,329 | 3/1981 | Ullman | 540/589 |
| 4,559,173 | 12/1985 | Flentge | 540/542 |

FOREIGN PATENT DOCUMENTS

| | | | |
|---|---|---|---|
| 56-87559 | 12/1979 | Japan. | |
| 57-109724 | 12/1980 | Japan | 540/589 |

OTHER PUBLICATIONS

Greene, Protective Groups in Organic Synthesis, (New York, Wiley and Sons, 1981), p. 183.
Grant and Hackh's Chemical Dictionary, (1987, New York, McGraw-Hill Books) pp. 14 and 219.

*Primary Examiner*—Mukund J. Shah
*Assistant Examiner*—Pavanaram K. Sripada
*Attorney, Agent, or Firm*—John R. Everett

[57] ABSTRACT

New carbamazepine hapten analogues are described comprising:

(A) an active ester group;

(B) a carbamazepine nucleus; and (C) a linking chain (i) linking the carboxamide group of the carbamazepine nucleus to the active ester group, said linking chain having about 4 to about 40 atoms consisting of:
  (1) alkylene groups; and
  (2) 5 to 7 membered heterocyclic ring groups, each group being joined into the linking group through chemical groups selected from
    (a) esters,
    (b) amides,
    (c) hetero atoms selected from —O—, —S—, and —NR—; wherein R represents hydrogen or $C_1$ to $C_6$alkyl; and
    (d) carbonyl groups.

The carbamazepine-active ester analogues are useful in preparing labeled carbamazepines. The labeled carbamazepines are useful in immunoassay elements and processes for the detection of carbamazepine drugs, for example, in body fluids.

3 Claims, No Drawings

CARBAMAZEPINE HAPTEN ANALOGUES

CROSS REFERENCE TO RELATED APPLICATIONS

Labeled Carbamazepine Hapten Analogues For Competitive Enzyme Imunoassays by Brummon, Saini 07/926,202, and Ponticello, and Immunoassays With Novel Labeled Carbamazepine Hapten Analogues by Brummond, Saini, and Ponticello, 07/926,203, filed on even date herewith.

FIELD OF THE INVENTION

This invention relates to clinical chemistry, particularly immunoassays.

BACKGROUND OF THE INVENTION

Immunoassays, which take advantage of natural immunological reactions, have found wide-spread use as analytical techniques in clinical chemistry. Because of the specificity of the reactions, they are particularly advantageous in quantifying biological analytes that are present in very low concentration in biological fluids. Such analytes (called ligands herein) include, for example, antigens, antibodies, therapeutic drugs, narcotics, enzymes, hormones, proteins, etc.

In competitive binding immunoassays, a labeled ligand, including immunocompetent derivatives and analogs of the ligand is placed in competition with unlabeled ligand for reaction with a fixed amount of the appropriate binding material (called a receptor herein). Unknown concentrations of the ligand can be determined from the measured signal of either the bound or unbound (i.e. free) labeled ligand. The reaction proceeds as follows:

ligand+labeled ligand+receptor→
ligand-receptor+labeled ligand-receptor.

Conventional labels include radioactive tags, enzymes, chromophores, fluorophores, stable free radicals, and enzyme cofactors, coenzymes, inhibitors and allosteric effectors.

Consistent with the foregoing an immunoassay for carbamazepine in serum can be based on competition of an enzyme labeled carbamazepine analogue with carbamazepine in the patient serum for immobilized antibody binding sites.

Specific requirements for the labeled carbamazepine analogue include: 1) at least about 70–90% of the analogue can be bound by excess immobilized carbamazepine antibody; 2) affinity of the analogue for immobilized antibody is such that competition of a fixed amount of analogue with carbamazepine occurs in a therapeutically relevant concentration range; and 3) stability of the labeled carbamazepine analogue against hydrolysis of its enzyme label under storage conditions. Requirements imposed on the carbamazepine derivative include: 1) accessibility of the derivative to the immobilized antibody following conjugation with the enzyme label; 2) specific recognition of the analogue by the carbamazepine antibody; and 3) sufficient reactivity of the derivative with the enzyme label, either directly or following activation of the enzyme or derivative, under conditions that do not adversely affect enzyme activity.

STATEMENT OF THE INVENTION

The present invention provides new carbamazepine analogues comprising:

(A) an active ester group such as succinimidoxycarbonyl;

(B) a carbamazepine nucleus;

(C) a linking chain (i) linking the carboxamide group of the carbamazepine nucleus to the active ester group through a carbonyl group and (ii) having about 4 to about 40 atoms consisting of:

(1) $C_2$ to $C_6$ alkylene groups; and
(2) 5 to 7 membered heterocyclic ring groups selected from 1,4-piperazinylene; 2,5'-dimethyl-1,4-piperazinylene; 1,3-imidazolidinylene, and 1,3-hexahydrodiazepinylene;

each group being joined into the linking group through chemical groups selected from (a) esters, including thioesters

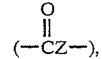

where Z is O or S;

(b) amides,

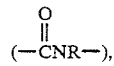

wherein R represents hydrogen or $C_1$ to $C_6$ alkyl (c) hetero atoms selected from —O—, —S—, and —NR—; wherein R represents hydrogen or $C_1$ to $C_6$ alkyl; and (d) carbonyl.

The drug hapten analogues defined above include those conforming to the structure (I):

Structure I

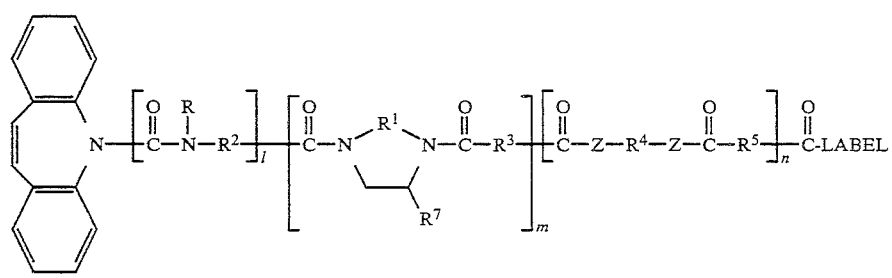

wherein

R is as previously defined;

$R^1$ represents alkylene of 1 to 3 carbon atoms sufficient to form with, $R^7$, a heterocylic group selected from 1,4-piperazinylene; 2,5'-dimethyl-1,4-piperazinylene; 1,3-imidazolidinylene, and 1,3-hexahydrodiazepinylene;

$R^2$, $R^3$, $R^4$ and $R^5$ each independently represent alkylene groups of about 2 to 10 carbon atoms such as methylene, ethylene, trimethylene, tetramethylene, pentylene or octylene, or phenylene; and $R^6$ represents ethylene or o-phenylene;

$R^7$ represents hydrogen or methyl;

each Z independently represents —O—, —S—, or preferably —NR— wherein R is as previously defined;

l represents 0, 1 or 2;

m is 0, 1, or 2;

n is 0, 1, or 2; and the sum of carbon and hetero atoms in the linking chain, comprising the atoms included in $R^2$ and in the brackets of m and n, is about 5 to 40 and further provided that (i) only one of $R^2$, $R^3$, $R^4$ or $R^5$ may be phenylene, (ii) the bracketed components, l, m and n can appear in any order.

Several advantages are realized by use of the drug hapten analogues of this invention. The active esters of the carbamazepine analogues having short linking chains between the carbamazepine nucleus and the active ester group were sufficiently reactive with HRP to prepare labeled drug hapten analogues for use with useful immobilized antibodies. Haptens with a longer linker between the active ester group and the carbamazepine nucleus gave labels that could be bound by all immobilized antibodies tested. Stability of the linking groups containing amide bonds are stable against hydrolysis.

We have prepared carbamazepine analogues containing active ester groups, especially succinimidoxycarbonyl groups, capable of rapidly and completely condensing with enzyme labels such as horseradish peroxidase (HRP). Other labels such as visible dyes, fluorescent dyes, radioactive materials, etc., can also be used by covalently bonding the labels to the analogues of this invention.

REDUCTION TO PRACTICE

The examples provided hereinafter illustrate the preparation of the new carbamazepine analogues of this invention.

Example 1—N-[2-(3-Succinimidoxycarbonyl-propionyloxy)ethyl]-carbamazepine

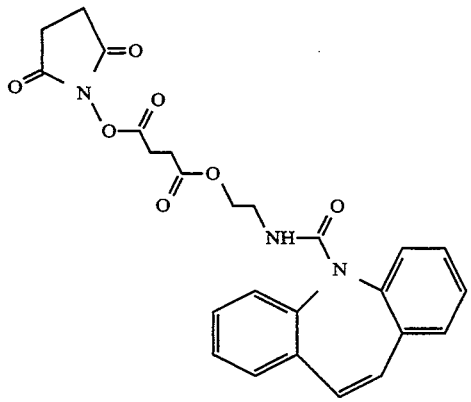

Step 1: Preparation of N-(2-Hydroxyethyl)-carbamazepine

A mixture of ethanolamine (6.1 g, 0.1 mole) and 5-chlorocarbonyl-2,2'-iminostilbene (6.5 g, 0.025 mole) in toluene (250 mL) was heated at reflux for 4 hours and then allowed to stand at ambient temperature for 16 hours. To the mixture was added dichloromethane (500 mL), and the solution was washed with 10% hydrochloric acid (2×100 mL), washed with saturated sodium bicarbonate solution (100 mL), washed with saturated sodium chloride solution (100 mL), dried over anhydrous magnesium sulfate, filtered, and the solvent removed on a rotary evaporator.

To the residue was added dichloromethane (45 mL) and ethyl acetate (75 mL), and the mixture was placed in the freezer (−16° C.). The solid was filtered.

Step 2: N-[2-(3-Carboxypropionyloxy)ethyl]-carbamazepine

A mixture of N-(2-hydroxyethyl)carbamazepine (5.6 g, 0.02 mole), succinic anhydride (2.2 g, 0.02 mole), and dimethylaminopyridine (2.4 g, 0.02 mole) in chloroform (25 mL) was stirred at ambient temperature for 24 hours. Dichloromethane (400 mL) was added, and the mixture was washed with 10% hydrochloric acid solution (2×100 mL), washed with saturated sodium chloride solution (100 mL), dried over anhydrous magnesium sulfate, filtered, and the solvent removed. To the residue was added ethyl ether (25 mL) and petroleum ether (25 mL). A sample was recrystallized from methanol.

Step 3: N-[2-(3-Succinimidoxycarbonylpropionyloxy)ethyl]carbamazepine

A mixture of N-[2-(3-carboxypropionyloxy)ethyl]-carbamazepine (3.8 g, 0.01 mole), N,N'-dicyclohexylcarbodiimide (2.1 g, 0.01 mole), and N-hydroxysuccinimide (1.2 g, 0.01 mole) in chloroform (75 mL) was stirred at room temperature for 20 hours. The mixture was filtered, and the filtrate was concentrated on a rotary evaporator in vacuo to give a white solid. Analytical calculated for $C_{25}H_{23}N_3O_7$: C, 62.89; H, 4.86; N, 8.80. Found C, 60.74: H, 5.12. N, 8.83.

Example 2—N-[3-(3-Succinimidoxycarbonyl-propionamido)-propyl]carbamazepine

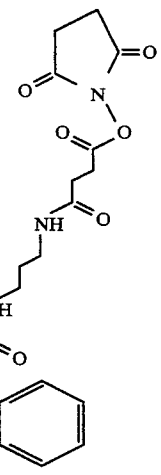

Step 1: N-[3-(Benzyloxycarbonylamino)propyl]-carbamazepine

A mixture of N-benzyloxycarbonyl-1,3-propanediamine (8.0 g, 0.04 mole) and triethylamine (5.0 g, 0.05 mole) in chloroform (75 mL) was added dropwise over 15 minutes to 5-chlorocarbonyl-2,2'-iminostilbene (7.6 g, 0.03 mole) in chloroform (200 mL). The mixture was then heated at reflux for 1 hour and at ambient temperature for 16 hours. Dichloromethane (500 mL) was added, and the mixture was washed with 10% hydrochloric acid (2×100 mL), washed with saturated sodium chloride solution (100 mL), dried over anhydrous magnesium sulfate, filtered, and the solvent removed on a rotary evaporator in vacuo. To the residue was added ethyl acetate (50 mL) and the solution placed in the freezer for 2 hours and filtered.

Step 2:N-(3-Aminopropyl)carbamazepine Hydrobromide

N-[3-(Benzyloxycarbonylamino)propyl]-carbamazepine (13.2 g, 0.03 mole) and 30–35% hydrogen bromide-acetic acid solution (70 mL) was allowed to stir at room temperature for 1 hour. This mixture was then poured into diethyl ether (3 L), and the solid which forms was triturated with fresh portions of ether (3×1 L). The solid was filtered.

Step 3: N-[3-(3-Carboxypropionamido)propyl]carbamazepine

A mixture of N-(3-aminopropyl)carbamazepine hydrobromide (7.5 g, 0.02 mole), triethylamine (2.0 g, 0.02 mole), and succinic anhydride (2.0 g, 0.02 mole) in chloroform (200 mL) was heated for 30 minutes at 50°–60° C. and allowed to stand at ambient temperature for 20 hours. Dichloromethane (500 mL) was added, and the mixture was washed with 10% hydrochloric acid (2×100 mL) and saturated sodium chloride solution (100 mL), then dried over anhydrous magnesium sulfate, filtered, and the solvent removed on a rotary evaporator in vacuo. To the residue was added dichloromethane (100 mL) and petroleum ether (100 mL), and it was placed in the freezer overnight. The solid was filtered.

Step 4: N-[3-(3-Succinimidoxycarbonylpropionamido)propyl]carbamazepine

A mixture of N-[3-(3-carboxypropionamido) propyl]-carbamazepine (3.3 g, 0.01 mole), N,N'-dicyclohexylcarbodiimide (2.0 g, 0.01 mole), and N-hydroxysuccinimide (1.0 g, 0.01 mole) in chloroform (80 mL) was stirred at room temperature for 20 hours. The mixture was filtered and the solvent removed on a rotary evaporator in vacuo to give 4.7 g. The solid was dissolved in dichloromethane (20 mL), filtered and the solvent removed. This procedure was repeated an additional time to give 3.0 g (64% yield). Analytical calculated for $C_{26}H_{26}N_3O_6$: C, 65.54; H, 5.50; N, 8.82. Found: C, 62,38; H, 5.47; N, 11.02.

Example 3—N-[3-(4-Succinimidoxycarbonylbutyramido)-propyl]carbamazepine

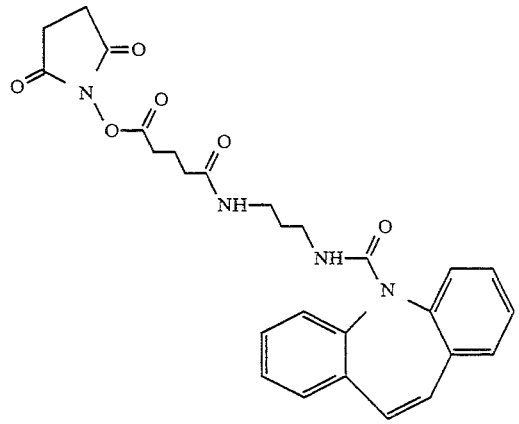

Step 1: N-[3-(4-Carboxybutyramido)propyl]carbamazepine

N-(3-aminopropyl)carbamazepine hydrobromide (4.8 g, 0. 0128 mole) was treated with glutaric anhydride (1.5 g, 0. 0128 mole), triethylamine (1.4 g, 0.014 mole) by the procedures described in step 3 of Example 2.

Step 2: N-[3-(4-Succinimidoxycarbonylbutyramido)-propyl]carbamazepine

N-[3-(4-Carboxybutyramido)propyl]-carbamazepine was treated with N-hydroxysuccinimide by the procedure described in step 4 of Example 2 to give the product. Analytical calculated for $C_{27}H_{28}N_4O_6$: C, 64.28; H, 5.59; N, 11.10. Found: C, 63.84; H, 5.72; N, 10.89.

Example 4—N-[6-(4-Succinimidoxycarbonylbutyramido)hexyl]carbamazepine

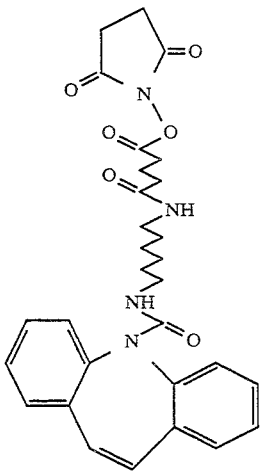

Step 1: N-[6-(Benzyloxycarbonylamino)hexyl]carbamazepine

This material was prepared using the procedure outlined in step 1, Example 2, except using N-benzyloxycarbonyl-1,6-hexanediamine in place of the N-benzyloxycarbonyl-1,3-propanediamine, to give 11.0 g (94% yield). Pure material was obtained by crystallization from ethyl acetate/pentane (1:1).

Step 2: N-(6-Aminohexyl)carbamazepine Hydrobromide

This material was prepared using the procedure outlined in Example 2, step 2, except substituting N-[6-(benzyloxycarbonylamino)hexyl]-carbamazepine for the N-[3-benzyloxycarbonylamino) -propyl]carbamazepine, to give 8.5 g (100% yield).

Step 3: N-[6-(4-Carboxybutyramido)hexyl]carbamazepine

This material was prepared using the procedure outlined in step 3, Example 2, except substituting N-(6-aminohexyl)carbamazepine hydrobromide and glutaric anhydride, respectively, for the N-(3-aminopropyl)carbamazepine hydrobromide and succinic anhydride. The product was crystallized from dichloromethane/ethyl acetate (1:1).

Step 4: N-[6-(4-Succinimidoxycarbonylbutyramido)hexyl]carbamazepine

This material was prepared using the procedure outlined in Example 2, step 4, except substituting N-[6-(4-carboxybutyramido)hexyl]carbamazepine for the N-[3-(3-carboxypropionamido)-propyl]carbamazepine. Analytical calculated for $C_{30}H_{34}N_4O_6$: C, 65,92; H, 6.27; N, 10.25. Found: C, 65.20; H, 6.19; N, 10.02.

Example 5—5-[4-(4-Succinimidoxycarbonylbutyryl)-piperazinocarbonyl]-5H-dibenzo[b,f]azepine

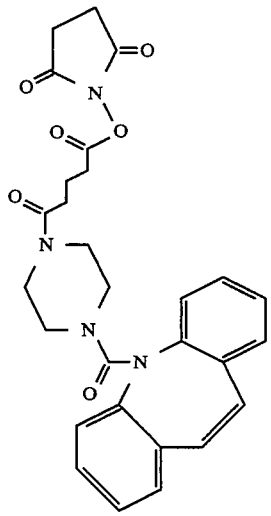

Step 1: 5-[4-(Benzyloxycarbonyl)piperazinocarbonyl]-5H-dibenzo[b,f]azepine

This material was prepared using the procedures outlined in Example 2, step 1, except substituting benzyl 1-piperazinecarboxylate in place of the N-benzyloxycarbonyl-1,3-propanediamine.

The compound was dissolved in ethyl ether (10 mL) and petroleum ether was added to the cloud point. The mixture was placed in a freezer and then filtered to give 9.3 g material.

Step 2A: 5-(Piperazinocarbonyl)-5H-dibenzo[b,f]azepine Hydrobromide

Step 2B: 5-[4-(4-Carboxybutyryl)piperazinocarbonyl]-5H-dibenzo[b, f]azepine

These materials were prepared using the procedures outlined in steps 2 and 3 of Example 2, except starting with 5-[4-(benzyloxycarbonyl)piperazinocarbonyl]-5H-dibenzo[b,f]azepine in place of the N-[3-(benzyloxycarbonylamino)propyl]carbamazepine in step 2, and thus the product 5-(Piperazinocarbonyl)-5H-dibenzo-[b,f]azepine Hydrobromide in place of the product of step 2, and glutaric anhydride in place of succinic anhydride in the procedures of step 3. The residue (2B) was crystallized from ethyl acetate (10 mL) and petroleum ether (2 mL), placed in a freezer, and filtered to give the acid.

Step 3: 5-[4-(3-Carboxypropionyl)piperazino-carbonyl]-5H-dibenzo[b,f]azepine

This material was prepared using the procedures outlined in step 2B of Example 4, except using succinic anhydride in place of glutaric anhydride. A sample recrystallized from dichloromethane/ethyl acetate (1:1) gave pure material.

Step 4: 5-[4-(4-Succinimidoxycarbonylbutyryl) piperazinocarbonyl]-5H-dibenzo[b,f]azepine This material was prepared using the procedure outlined in Example 2, step 4, except using 5-[4-(carboxybutyryl) piperazinocarbonyl]-5H-dibenzo-[b,f]azepine in place of the N-[3-(3-carboxypropionamido) propyl]-carbamazepine to give 4.6 g ( 100% yield). The material (3.0 g) was chromatographed using silica gel. Analytical calculated for $C_{28}H_{28}N_4O_6$: C, 65.09; H, 5.47; N, 10.85. Found: C, 64.87; H, 5.99; N, 10.62.

Example 6-5-[4-(3-Succinimidoxycarbonylpropionyl)-piperazinocarbonyl]-5H-dibenzo[b,f]azepine

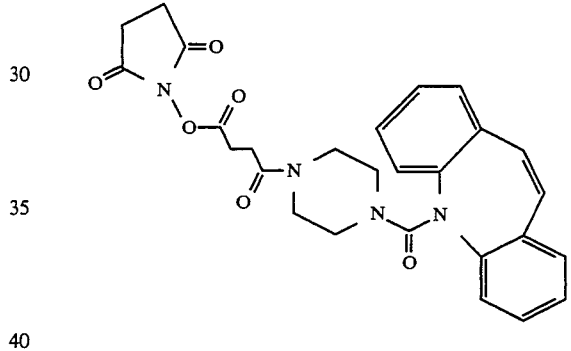

This material was prepared using the procedure outlined in step 4, Example 2, except using 5-[4-(3-carboxypropionyl)piperazinocarbonyl]-5H-dibenzo [b,f]azepine in place of the N-[3-(3-carboxypropionamido)propyl]-carbamazepine. A sample was recrystallized from dichloromethane (35 mL) and ethyl acetate (8 mL) to give material melting at 135°–140° C. Analytical calculated for $C_{27}H_{26}N_4O_6$: C, 64.33; H, 5.22; N, 11.15. Found: C, 62.46; H, 5.29; N, 10.82.

Example 7—N-(4-Succinimidoxycarbonylbutyl)carbamazepine

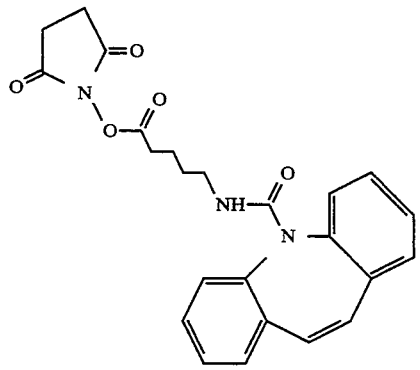

Step 1: N-(4-Methoxycarbonylbutyl)carbamazepine

To a mixture of sodium hydride (6.0 g, 0.2 mole, 80%) and carbamazepine (40.0 g, 0.17 mole) in tetrahydrofuran (400 mL) was added over 30 minutes methyl 5-bromovalerate (39.0 g, 0.19 mole) in tetrahydrofuran (100 mL). The mixture was stirred at ambient temperature for 3 days and then poured into ice containing concentrated hydrochloric acid (100 mL). The aqueous solution was extracted with dichloromethane (3×200 mL), and the combined organic solutions were washed with saturated sodium bicarbonate solution (200 mL), saturated sodium chloride solution (200 mL), then dried over anhydrous magnesium sulfate, filtered, and the solvent removed on a rotary evaporator in vacuo. To the residue was added ethyl ether (100 mL). The mixture was placed in the freezer (−16° C.) and filtered to give a white solid.

Step 2: N-(4-Carboxybutyl)carbamazepine

N-(4-Methoxycarbonylbutyl)carbamazepine (6.3 g, 0.18 mole) was dissolved in p-dioxane (120 mL), water (25 mL), and concentrated hydrochloric acid (50 mL). The solution was refluxed for 2 hours and then stirred to ambient temperature. To this mixture was added saturated sodium chloride solution (100 mL) and the mixture extracted with dichloromethane (3×300 mL). The combined organic solutions were washed with saturated sodium chloride solution (100 mL), dried over anhydrous magnesium sulfate, filtered, and the solvent removed. The residue was dissolved in dichloromethane (175 mL) and ethyl acetate (100 mL) was added. The mixture was placed in the freezer (−16° C.) and then filtered.

Step 3: N-(4-Succinimidoxycarbonylbutyl)carbamazepine

This material was prepared using the procedure outlined in Example 2, step 4, except using N-(4-carboxybutyl)carbamazepine in place of the N-[3-(3-carboxypropionamido)propyl]carbamazepine. Analytical calculated for $C_{24}H_{23}N_3O_5$: C, 66.50; H, 5.35; N, 9.69. Found: C, 65.82; H, 5.58; N, 9.37.

Example 8—N-{4-[4-(3-Succinimidoxycarbonylpropionyl)piperazinocarbonyl]butyl}-carbamazepine Step 1:N-[4-(4-Benzyloxycarbonylpiperazino-carbonyl butyl]carbamazepine A mixture of N-(4-carboxybutyl)carbamazepine (3.4 g, 0.01 mole) and 1,1′-carbonyldiimidazole (2.1 g, 0.0125 mole) in tetrahydrofuran (100 mL) was stirred at ambient temperature for 30 minutes. To this mixture was added at room temperature over 30 minutes benzyl 1-piperazinecarboxylate (2.75 g, 0.0125 mole) in tetrahydrofuran (100 mL). After 20 hours, dichloromethane (300 mL) was added, and the organic solution was washed with 5% hydrochloric acid solution (3×100 mL), washed with saturated sodium carbonate solution (100 mL), washed with saturated sodium chloride solution (100 mL), dried over anhydrous magnesium sulfate, filtered, and the solvent removed on a rotary evaporator in vacuo. The material was used directly in the next step.

Step 2A: N-(4-Piperazinocarbonylbutyl)carbamazepine Hydrobromide

Step 2B: N-{4-[4-(3-Carboxypropionyl)-piperazinocarbonyl]butyl}carbamazepine

These materials were prepared using the procedures outlined in steps 2 and 3 of Example 2, except starting with N-[4-(4-benzyloxycarbonylpiperazinocarbonyl)butyl]carbamazepine in place of the N-[3-(benzyloxycarbonylamino)propyl]carbamazepine in step 2A, and then using the product from step 2A of Example 8 in place of the product of step 2 of Example 2 in step 2B of Example 8 to give the acid.

Step 3: N-{4-[4-(3-Succinimidoxycarbonylpropionyl)piperazinocarbonyl]butyl}carbamazepine This material was prepared using the procedure outlined in Example 2, step 4, except using N-{4-[4-(3-carboxypropionyl)piperazinocarbonyl]butyl}carbamazepine in place of the N-[3-(3-carboxypropionamido)propyl]carbamazepine. A sample was chromatographed using silica gel to give analytically pure material. Analytical calculated for $C_{32}H_{35}N_5O_7$: C, 63.88; H, 5.86; N, 11.64. Found: C, 63.13; H, 6.02; N, 11.06.

Example 9—N-{4-[3-(4-Succinimidoxycarbonylbutyramido) propylaminocarbonyl]butyl}carbamazepine Step 1: N-[4-(3-Benzyloxycarbonylaminopropylaminocarbonyl)butyl]carbamazepine This material was prepared using the procedure outlined in step 1 of Example 8, except substituting N-benzyloxycarbonyl-1,3-propanediamine for the benzyl 1-piperazinocarboxylate. The residue was treated with ethyl ether (8 mL), acetone (4 mL), and petroleum ether (3 mL), placed in a freezer (−16° C.), and filtered to give the product.

Step 2A: N-[4-(3-Aminopropylaminocarbonyl)butyl]carbamazepine Hydrobromide

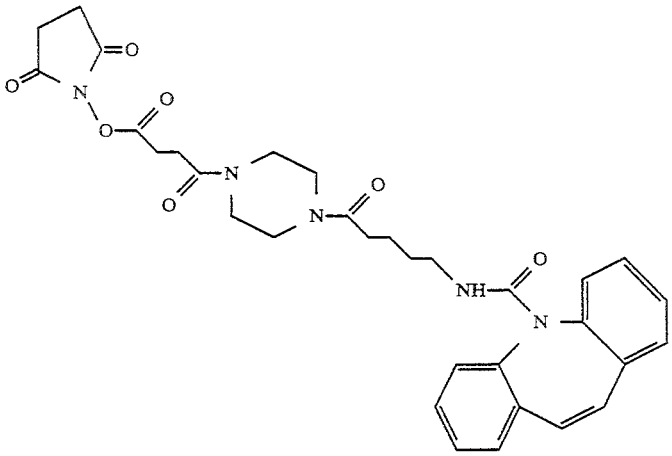

Step 2B: N-{4-(3-(4-Carboxybutyramido)-propylaminocarbonyl]butyl}carbamazepine

These materials were prepared using the procedures outlined in steps 2 and 3 of Example 2, except substituting N-[4-(3-benzyloxycarbonylaminopropylaminocarbonyl) butyl]carbamazepine in place of the N-[3-(benzyloxycarbonylamino)propyl]carbamazepine in step 2, and N-[4-(3-aminopropylaminocarbonyl) butyl]carbamazepine hydrobromide for the N-(3-aminopropyl)-carbamazepine hydrobromide and glutaric anhydride for the succinic anhydride in step 3, to give 2.6 g (44%) yield. The solid was recrystallized from methanol (4 mL) and ethyl acetate (15 mL) to give pure material.

Step 3: N-{4-[3-(4-Succinimidoxycarbonyl-butyramido) propylaminocarbonyl]butyl}carbamazepine This material was prepared using the procedures outlined in step 4 of Example 2, except substituting N-{4-[3-(4-carboxybutyramido)propylaminocarbonyl]-butyl}carbamazepine for the N-[3-(3-carboxypropionamido) propyl]carbamazepine. A sample was chromatographed on silica gel to give a white solid. Analytical calculated for $C_{32}H_{37}N_5O_7$: C, 63.67; H, 6.18; N, 11.60. Found: C, 61.74; H, 6.21; N, 10.77.

The invention has been described in detail with particular reference to preferred embodiments thereof, but it will be understood that variations and modifications can be effected within the spirit and scope of the invention.

What is claimed is:

1. A carbamazepine analogue conforming to the structure:

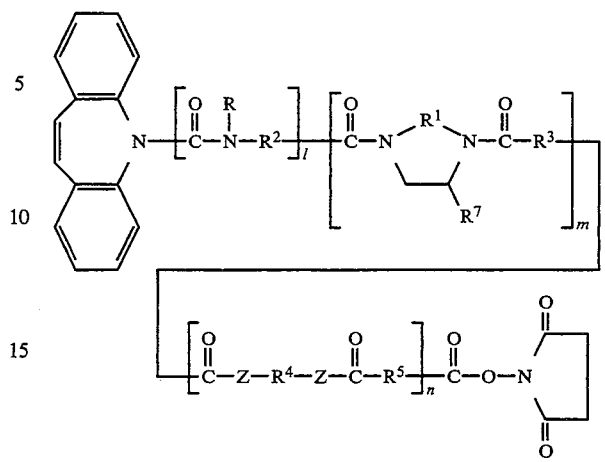

wherein:
R is hydrogen or $C_1$-$C_6$ alkyl;
$R^1$ represents alkylene of 1 to 3 carbon atoms sufficient to form with $R^7$ a heterocyclic group selected from 1,4-piperazinylene; 2,5-dimethyl-1,4-piperazinylene; 1,3-imidazolidinylene, and 1,3-hexahydrodiazepinylene;
$R^2$, $R^3$, $R^4$ and $R^5$ each independently represent alkylene and phenylene groups; and
each Z independently represents —O—, —S—, or preferably —NR— wherein R is as previously defined;
l represents 0, 1 or 2;
m is 0, 1, or 2;
n is 0, 1, or 2; and
the sum of carbon and hetero atoms in the linking chain, comprising the atoms included in $R^2$ and in the brackets of m and n, is about 5 to 40 and further provided that (i) only one of $R^2$, $R^3$, $R^4$ and $R^5$ may be phenylene and (ii) the bracket components, l, m and n can appear in any order.

2. The drug hapten analogue derivatives of claim 1 according to structure I wherein
$R^1$ represents ethylene thereby forming, with the atoms to which it is bonded, a 1,4-piperazinylene ring group; and
$R^2$, $R^3$, $R^4$, and $R^5$ each independently, represents methylene, ethylene, trimethylene, tetramethylene or pentylene;

3. The analogue according to claim 1, structure I selected from:
N-[2-(3-Succinimidoxycarbonylpropionyloxy)ethyl]-carbamazepine;
N-[3-(3-Succinimidoxycarbonylpropionamido)-propyl]carbamazepine;
N-[3-(4-Succinimidoxycarbonylbutyramido)propyl]-carbamazepine;
N-[6-(4-Succinimidoxycarbonylbutyramido)hexyl]-carbamazepine;
N-(4-Succinimidoxycarbonylbutyl)carbamazepine;
5-[4-(4-Succinimidoxycarbonylbutyryl)-piperazinocarbonyl ]-5H-dibenzo[b,f]azepine;
5-[4-(3-Succinimidoxycarbonylpropionyl)-piperazinocarbonyl ]-5H-dibenzo[b,f]azepine;
N-{4-[4-(3-Succinimidoxycarbonylpropionyl)-piperazinocarbonyl ]butyl}carbamazepine;
N-{4-[3-(4-Succinimidoxycarbonylbutyramido)-propylaminocarbonyl ]butyl}carbamazepine.

* * * * *